United States Patent [19]

Blake

[11] 4,007,743
[45] Feb. 15, 1977

[54] OPENING MECHANISM FOR UMBRELLA-LIKE INTRAVASCULAR SHUNT DEFECT CLOSURE DEVICE

[75] Inventor: Larry W. Blake, Costa Mesa, Calif.

[73] Assignee: American Hospital Supply Corporation, Evanston, Ill.

[22] Filed: Oct. 20, 1975

[21] Appl. No.: 623,788

[52] U.S. Cl. .......................... 128/334 R; 128/334 C
[51] Int. Cl.² ........................................ A61B 17/04
[58] Field of Search ........... 128/334 R, 334 C, 335, 128/242–244, 345, 356; 135/20, 22–24

[56] References Cited

UNITED STATES PATENTS

| | | |
|---|---|---|
| 3,540,431 | 11/1970 | Mobin-Uddin ................... 128/1R |
| 3,844,302 | 10/1974 | Klein ................................. 135/26 |
| 3,874,388 | 4/1975 | King et al. ................. 128/334 C X |

Primary Examiner—Dalton L. Truluck

[57] ABSTRACT

The pivotable struts of an umbrella-like shunt defect closure device are resiliently biased from a collapsed position to an expanded position by resilient and foldable flat ring sections which extend between the struts when the struts are in their expanded positions but which are folded between the struts when the struts are in their collapsed positions.

14 Claims, 9 Drawing Figures

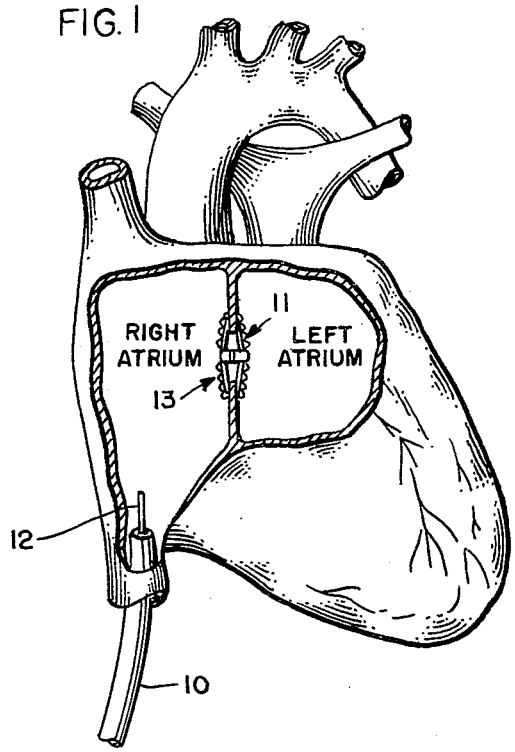
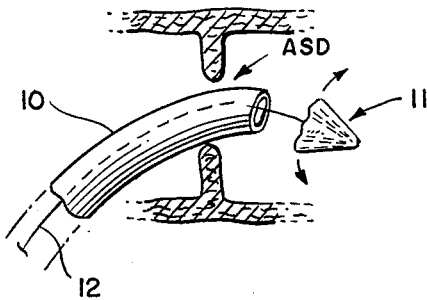
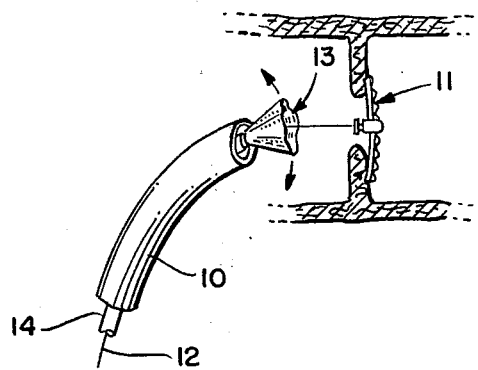
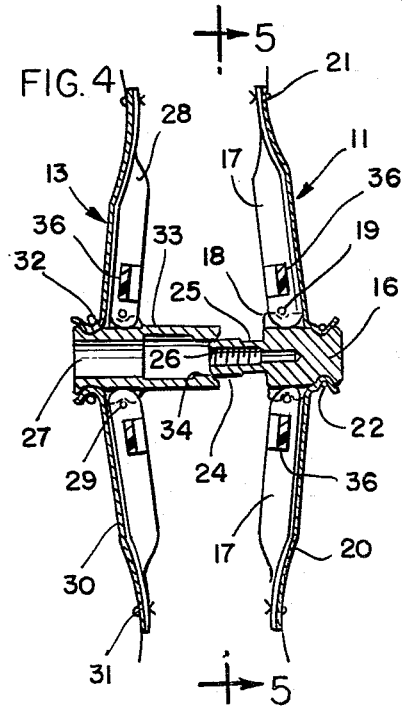
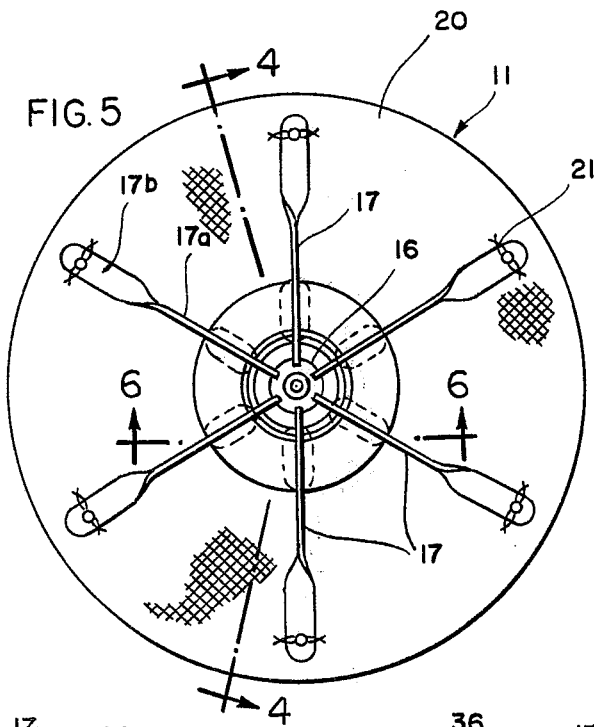
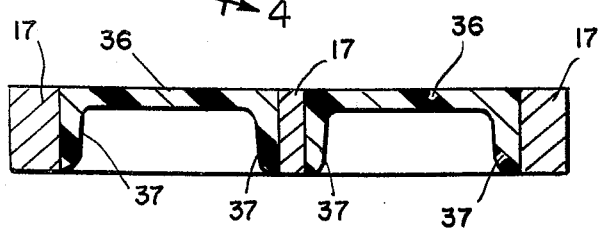

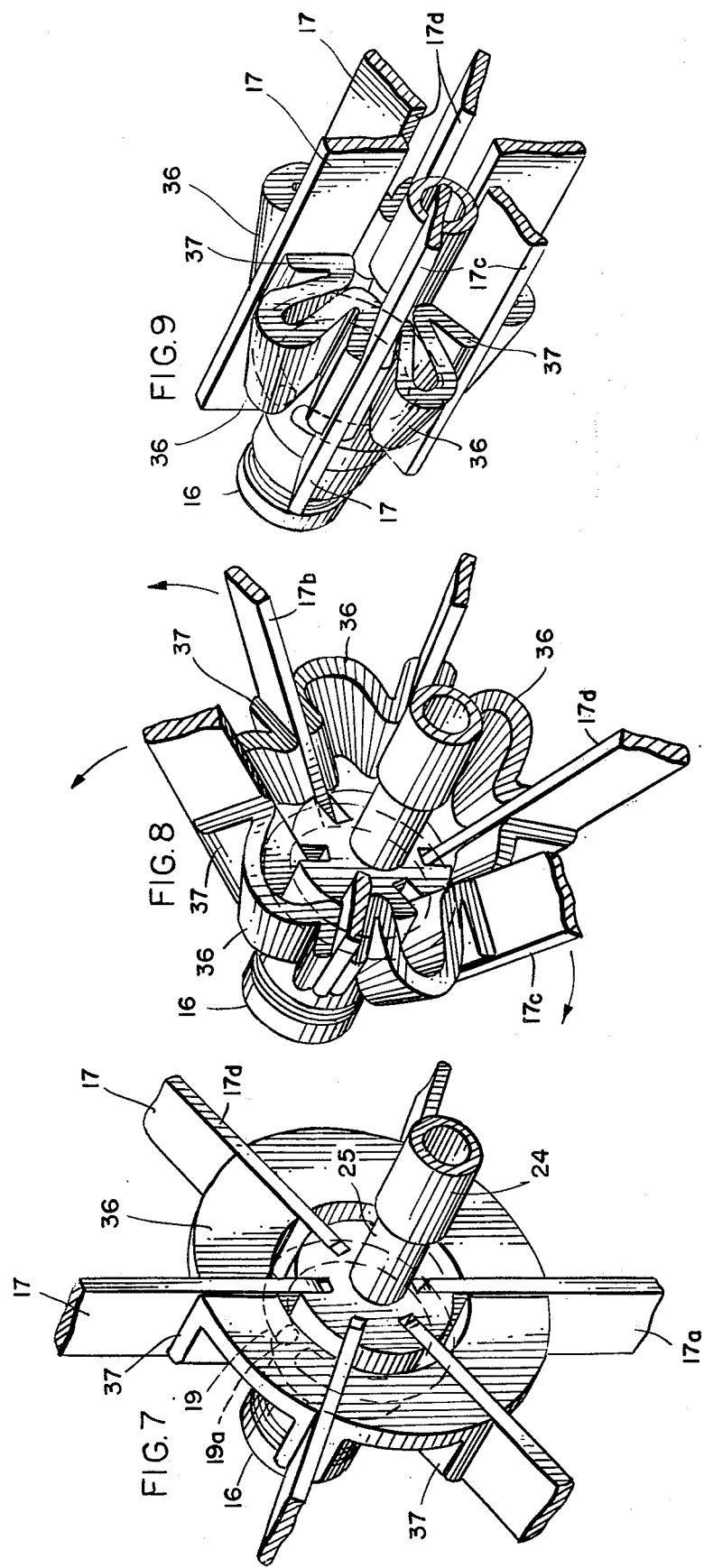

OPENING MECHANISM FOR UMBRELLA-LIKE INTRAVASCULAR SHUNT DEFECT CLOSURE DEVICE

BACKGROUND

This invention relates to an opening mechanism for an intravascular shunt defect closure device such as described in U.S. Pat. No. 3,874,388. As explained in the patent, abnormal openings, holes, or shunts can occur between the chambers of the heart or the great vessels (interatrial and interventricular septal defects or patent ductus arteriosus and aorthico-pulmonary window respectively), causing shunting of blood through the opening. The deformity is usually congenital, resulting from a failure of completion of the formation of the septum, or wall, between the two sides during fetal life when the heart forms from a folded tube into a four-chambered, two unit system.

The patent describes a device and method for closing such defects without open-heart surgery. The devices described in the patent are similar to an umbrella and include a central hub and a plurality of struts which are pivotally mounted on the hub. A disc of sheet material such as Dacron or the like is attached to the struts, and the struts are pivotable from a collapsed or closed position in which the struts extend generally parallel to the axis of the hub to an expanded or open position in which the struts extend generally perpendicularly to the axis of the hub. When the struts are in the open position, the Dacron disc is maintained generally flat and is moved into position to close the shunt.

The patent describes shunt closure devices for closing an atrial septal defect (ASD), a ventricular septal defect (VSD), and a patent ductus arteriosus (PDA). In each case the umbrella-like closure device is located in position to close the defect by inserting a catheter which carries the collapsed device into the heart. The device is then pushed out of the catheter and caused to expand by opposing forces exerted on the device by an inner catheter and, in the case of a left atrial or ventricular defect, an obturator wire or, in the case of a right atrial or ventricular defect, retraction ties or elevating struts.

SUMMARY

The expansion means of the invention simplifies the opening of the umbrella-like shunt closure device, improves its reliability, and decreases its cost. The resilient ring sections automatically open the struts to their fully open position as the device is pushed out of the catheter, and no additional manipulation is required to expand the umbrella. Since each strut is connected to the adjacent struts on each side by a ring section, a strut which for some reason resists movement into its expanded position tends to be pulled into that position by the strips which join it to neighboring struts. The ring sections are molded in place between the expanded struts and securely fastened to the struts by adhesive. The resilient ring sections will therefore always tend to return to their original, flat positions and open the struts as soon as the collapsing force exerted by the catheter is removed.

DESCRIPTION OF THE DRAWING

The invention will be explained in conjunction with an illustrative embodiment shown in the accompanying drawing, in which FIG. 1 is a schematic illustration of the heart, partially broken away, showing a pair of umbrella-like closure devices closing an atrial septal defect;

FIG. 2 is a schematic illustration of one of the umbrella-like closure devices being pushed from the catheter into the left atrium and in the process of expanding from its closed position to its open position;

FIG. 3 is a schematic illustration similar to FIG. 2 showing the first closure device positioned in the left atrium and a second umbrella-like closure device being pushed from the catheter and in the process of opening;

FIG. 4 is an enlarged axial sectional view of the two closure devices of FIG. 3 in the process of being interconnected at their hubs;

FIG. 5 is a plan view of one of the closure devices taken along the line 5—5 of FIG. 4;

FIG. 6 is an enlarged fragmentary sectional view taken along the line 6—6 of FIG. 5;

FIG. 7 is an enlarged fragmentary perspective view of the closure device of FIG. 5, with the closure material removed from the struts for clarity of illustration, showing the struts in their open or expanded position;

FIG. 8 is a view similar to FIG. 7 showing the struts in a partially opened position; and FIG. 9 is a view similar to FIGS. 7 and 8 showing the struts in a collapsed or closed position.

DESCRIPTION OF SPECIFIC EMBODIMENT

FIGS. 1–3 illustrate the method of closing an atrial septal defect with a pair of umbrella-like closure devices. This method is described in U.S. Pat. No. 3,874,388 with respect to the closure devices described therein, and the manipulative steps for positioning the closure devices is similar to the method used with closure devices provided with the inventive opening mechanism.

An ASD is closed by making an incision in the right or left groin and inserting a catheter 10 into the right atrium of the heart via the femoral vein. The catheter is further advanced until it extends through the ASD into the left atrium. A left side closure device 11 (FIG. 2) which is stored in a collapsed position within the catheter is then pushed out of the catheter by an obturator wire 12 which is threadedly engaged with the hub of the closure device. As soon as the closure device is pushed out of the catheter, the opening mechanism, which will be described in detail hereinafter, opens the umbrella-like device into the fully open position illustrated in FIGS. 1 and 4. The left side device 11 is shown in FIG. 2 in the process of opening, but it will be understood that the device opens almost immediately upon becoming free of the catheter.

After the left side device 11 is opened, the catheter 10 is withdrawn into the right atrium, and the closure device is pulled against the atrial septum by the obturator wire 12.

A right side closure device 13, which is also stored in the catheter in a collapsed position, is then pushed out of the catheter 10 by an inner catheter 14 having a smaller diameter than the outer catheter 10. The hub of the right side closure device 13 is provided with a central opening through which the obturator wire extends so that the closure device can be pushed along the wire by the inner catheter. As soon as the outer ends of the struts of the right closure device move past the end of the outer catheter, the opening mechanism of the invention moves the struts outwardly toward the open position. The right closure device 13 is shown in the process of opening in FIG. 3, but it will be understood that the device is opened substantially simultaneously as it clears the end of the catheter. After the right closure device is opened, it is pushed against the atrial septum until the hubs of the devices interconnect as shown in FIG. 1. The obturator wire is then unscrewed from the left closure device 11, and the obturator wire and catheter are withdrawn from the right atrium, leaving the interconnected closure devices 11 and 13 in position closing the ASD.

Referring now to FIGS. 4 and 5, the left closure device 11 includes a central hub 16 and a plurality of struts 17 which are pivotally mounted in the hub at circumferentially spaced locations. The hub is provided with an axially extending groove 18 for each of the struts, and the inner end of each strut is pivotally retained within one of the grooves by a ring 19 (see also FIG. 7) which is positioned within a circumferentially extending groove in the hub. The ring is interrupted at 19a in FIG. 7 to permit the struts to be inserted into the grooves 18 by positioning the ends of the ring on opposite sides of the groove, inserting the strut, and then rotating the ring through the pivot opening of the strut. In the particular embodiment illustrated, the left closure device includes six struts which are spaced 60° apart around the periphery of the hub.

Each strut includes a first or inner portion 17a which is generally flat and which includes generally parallel flat side surfaces which extend parallel to a plane defined by the open strut and the axis of the hub. The outer end portion 17b is twisted 90° relative to the inner portion 17a to provide a flat surface to which the disc 20 of closure material can be secured. The closure material can be Dacron or any other material suitable for intracardiac use and is attached to the end of each strut by a pair of ties 21 which are passed through an opening in the end of the strut and the closure material. The ties can be formed of Dacron yarn or similar material, and the ends of the ties can be fused together on the inside surface of the device which is shown in FIG. 5. The disc is provided with a central opening through which the outer end of the hub 16 extends, and the periphery of the central opening is secured to the hub by a thread 22 of Dacron or the like which tightly retains the closure material in a groove formed in the hub.

The inner end of the hub 16 terminates in a connector portion 24 of reduced diameter, and a locking groove 25 is provided between the connector portion 24 and the enlarged main body of the hub. An internally threaded opening 26 extends into the connector portion for attaching the threaded end of the obturator wire 12 to the hub 16.

The right closure device 13 is similar to the left closure device, but the hub 27 thereof is somewhat different. The right closure device includes struts 28 which are identical to the struts 17 and which are pivotally retained within grooves in the hub 27 by pivot ring 29. A disc 30 similar to the disc 20 is secured to the outer ends of the struts by ties 31, and the periphery of the inner opening of the disc is secured to the hub 27 by a tie 32 which retains the closure material within a groove in the hub. The hub 27 is provided with an axially extending central opening, and the inner end of the hub terminates in axially extending connecting fingers 33, each of which includes a radially inwardly extending locking shoulder 34. The locking fingers 33 can be formed by slitting the hub 27 at circumferentially spaced locations to provide separate, resilient fingers.

The inside diameter formed by the fingers is normally less than the outside diameter of the connecting portion 24 of the hub of the left closure device, and the inner ends of either or both of the connecting portion 24 or the connecting fingers 33 are provided with camming surfaces to permit the fingers to be forced outwardly as the closure devices are moved together and the fingers contact the connecting portion as illustrated in FIG. 4. As the closure devices are forced together, the resilient fingers will eventually snap the locking shoulders 34 into the groove 25 of the hub 16, thereby interconnecting the two closure devices. The interconnected devices are shown in FIG. 1, and in this position the struts of the two closure devices press against opposite sides of the atrial septum, and the Dacron discs thereof close the ASD.

The opening mechanism for opening each of the closure devices as it clears the catheter 10 will be described with reference to the left closure device 11, but the right closure device 13 includes an identical opening mechanism. Referring to FIGS. 5–7, a flat strip 36 extends between each pair of adjacent struts 17 at a location spaced outwardly from the pivot points of the struts. In the embodiment illustrated, each of the flat strips 36 extends generally arcuately between two struts and terminates in right angle attaching legs 37 which are secured to the flat side surfaces of the struts.

When the struts are in the open or expanded position illustrated in FIGS. 5 and 7, the struts extend generally radially outwardly from the hub 16, and the flat strips 36 lie generally in a plane which extends perpendicularly to the flat side surfaces of the struts and to the axis of the hub. Each of the strips 36 extend arcuately between the struts to which it is attached and form an interrupted ring or annulus. The strips can therefore be considered as segments or sections of an annularly shaped ring or band or as sectors of an annulus.

The strips 36 are formed of foldable, resilient material such as silicone rubber, and the strips are sized and positioned so that they are substantially unstressed when the struts are in the open position as in FIG. 7. The preferred method of forming the strips is to mold the plastic strips between the open struts while simultaneously adhesively securing the strips to the struts with silicone-to-metal adhesive. The molding operation insures that the resilient strips will be in a relaxed, unstressed condition when the struts are open. However, the strips can also be preformed and secured to the open struts by adhesive or the like.

The closure device is illustrated in a collapsed or closed position in FIG. 9. This is the position which the closure device occupies within the catheter 10, and the struts are retained in the collapsed position by the wall of the catheter. As the struts are pivoted downwardly from the open position of FIG. 7 to the closed position of FIG. 9 in order to insert the closure device into the catheter, the flat strips 36 are forced to fold outwardly into a generally U shape as shown in FIG. 8. When the struts reach the fully closed position of FIG. 9, the attaching ends 37 of each strip are positioned adjacent each other, and the strip is folded on itself into a compact configuration.

The folding of the resilient strips is resisted by the resilience of the material and creates a force within each strip which tends to return the strip to its original, flat configuration shown in FIG. 7. The strip can return to its unstressed flat configuration only if the distance between the struts to which it is attached increases, and the only way that this distance can increase is if the struts pivot outwardly toward the open position. The tendency of the strips to return to their original configuration therefore exerts an opening force on each of the struts.

The opening force exerted on the struts is resisted by the catheter so long as the closure device is retained within the catheter. However, as soon as the closure device is pushed beyond the catheter, the resilient strips will immediately spring the struts outwardly into the open position of FIG. 7. The closure device is therefore reliably opened as soon as it leaves the catheter without any additional manipulative steps.

When the struts are in the closed position, each of the folded strips exerts an unfolding force in a direction generally parallel to a tangent to the periphery of the hub midway between the two associated struts. The flat side surfaces of the struts form an acute angle to the direction of this force, and the force exerted or each of the struts can therefore be resolved into a component which extends parallel to the side surfaces of the strut and generally radially outwardly from the hub and a component which extends perpendicularly to the side surfaces of the strut. The radially outwardly directed component urges the strut to pivot outwardly to the open position.

The resilient strips cause expansion of the struts not only by reason of the unflexing or spreading action of each strip as it returns to its flat untensioned state, but also because the multiple struts are in effect ganged together by the interconnecting strips or webs. If for any reason one of the struts resists (or is restrained from) moving into its expanded position, that strut will tend to be pulled into erected position by the already-expanded (or expanding) neighboring struts which are connected to the balking strut by the resilient strips. This pulling action results from the fact that the shortest distance between an open strut and an adjacent strut occurs when the adjacent strut is also in an open position, and the length of the strip corresponds to this shortest distance. It is believed apparent that such cooperative pulling action of the strips, along with the individual unflexing or spreading action of each strip, contributes to reliability and dependability of operation in a device where failure of one or more of the struts to open could have serious consequences, i.e., the need for open-heart surgery to remove or adjust the malfunctioning device.

As shown in FIGS. 8 and 9, each strip or web arches radially outwardly as it is folded. Such outward folding occurs (in contrast to inward folding or random buckling) because, when the struts are collapsed (FIG. 9), the outermost edges 17c of a pair of adjacent struts are spaced further apart than the innermost edges 17d of those same struts, whereas such spacing is equal when the struts are expanded (FIG. 7). Thus, as the struts are pivoted inwardly into collapsed condition, a twisting or turning force is applied to each strip 36 to cause it to bow outwardly in the manner depicted in FIG. 8. Since the strips when fully expanded lie along a plane immediately adjacent edges 17d of the struts (FIG. 7), and spaced from edges 17c, the outward folding of each strip is at least partially accommodated, and is preferably entirely accommodated, within the space between adjacent struts. In other words, the fully folded strips or webs do not project ourwardly to any appreciable extent beyond edges 17c when the struts are collapsed (FIG. 9).

The twisted outer end portions 17b of the struts also contribute to the compact configuration of the collapsed closure device. These twisted end portions are substantially parallel to the septum when the open device is positioned to close the septal defect, and the end portions of the opposed closure devices can flex somewhat away from each other to accommodate differences in septum thickness. The flat end portions also decrease the possibility of the struts cutting into the septum.

Although the strips 36 in the specific embodiment illustrated extend arcuately between adjacent struts, it will be understood that other shapes of strips can be used. For example, each strip can extend in a straight line between adjacent struts so that the several strips form an outline of a polygon. Further, although the strips 36 have a flat cross section, strips of other cross sections, such as circular, will provide a similar opening force on the struts when folded between the closed struts. I have found it advantageous to mold the strips in place between the open struts, and as a result the strips are unstressed when the struts are open. However, the strips can be formed so that they still are somewhat folded even when the struts are open in order to insure that the strips will exert a sufficient force to fully open the struts.

While in the foregoing specification a detailed description of a specific embodiment of the invention was set forth for the purpose of illustration, it is to be understood that many of the details hereingiven may be varied considerably by those skilled in the art without departing from the spirit and scope of the invention.

I claim:

1. In an umbrella-like expansive device for closing intravascular shunt defects and the like, said device having a central hub, a plurality of struts movably mounted on the hub and movable between a first, collapsed position in which the struts extend generally parallel to the axis of the hub and a second, expanded position in which the struts extend generally radially from the hub, and closure material extending between the struts and secured thereto, an improved expansion means for moving the struts from the first position to the second position comprising a foldable, resilient strip extending between each pair of adjacent struts and secured thereto, each strip being folded between the struts when the struts are in the first position, whereby the folded resilient strips bias the struts from the first position toward the second position.

2. The structure of claim 1 in which each of the strips is generally flat when the struts are in the second position.

3. The structure of claim 1 in which each of the strips extends generally arcuately between its associated struts in a plane which extends through the associated adjacent struts when the struts are in the second position.

4. The structure of claim 3 in which each of the strips has a shape corresponding generally to a sector of an annulus when the associated struts are in the second position.

5. The structure of claim 4 in which each of the strips is generally flat when the struts are in the second position.

6. The structure of claim 4 in which the strips form an annulus which is interrupted by the struts.

7. The structure of claim 1 in which the strips are formed of silicone rubber.

8. The structure of claim 1 in which each of the strips is formed of silicone rubber and is adhesively joined to its associated struts.

9. The structure of claim 1 in which each of the strips are folded into a general U-shape which extends outwardly from the axis of the hub when the struts are in the first position.

10. The structure of claim 1 in which each of the struts are pivotally mounted on the hub for pivoting about an axis which is spaced from and extends perpendicularly to the axis of the hub and each strut includes a pair of generally parallel side surfaces which extend generally perpendicularly to the pivot axis of the strut, each of said strips including a pair of end portions which are secured to the side surfaces of adjacent struts, the end portions of each strip extending generally perpendicularly to the adjacent portion of the strip when the associated struts are in the second position.

11. In an intravascular shunt defect closure device for closing a shunt defect having a central hub and a plurality of struts pivotally mounted on the hub, each of the struts being pivotable about an axis which is spaced from and extends perpendicularly to the axis of the hub and being pivotable from a first, collapsed position in which the strut extends generally parallel to the axis of the hub and a second, expanded position in which the strut extends generally perpendicularly to the axis of the hub, an improved expansion means for moving the struts from the first position to the second position comprising an arcuately shaped foldable and resilient ring section extending between each pair of adjacent struts and secured thereto at points spaced from the pivot points of the struts, each ring section having a shape corresponding generally to a sector of an annulus and being substantially flat when the associated struts are in the second position and being folded into a general U-shape which extends outwardly from the axis of the hub when the struts are in the first position whereby the folded resilient ring sections bias the struts from the first position to the second position.

12. The structure of claim 11 in which each of the ring sections is formed of silicon rubber and is adhesively joined to its associated struts.

13. The structure of claim 11 in which each of the struts includes a bottom edge which extends adjacent to and generally parallel to the hub axis when the strut is in the first position, a top edge, and a pair of generally parallel flat side surfaces, each of the ring sections being secured to the associated struts adjacent the bottom edges thereof.

14. The structure of claim 10 in which each of the struts includes a pair of generally parallel side surfaces which extend generally perpendicularly to the pivot axis of the strut, each of the ring sections including a pair of end portions which are secured to the side surfaces of adjacent struts, the end portions of each ring section extending generally perpendicularly to the adjacent portion of the ring section when the associated struts are in the second position

* * * * *

UNITED STATES PATENT AND TRADEMARK OFFICE
CERTIFICATE OF CORRECTION

PATENT NO. : 4,007,743

DATED : February 15, 1977

INVENTOR(S) : Larry W. Blake

It is certified that error appears in the above–identified patent and that said Letters Patent are hereby corrected as shown below:

In column 8, line 22, "10" should be --11--.

Signed and Sealed this

Nineteenth Day of April 1977

[SEAL]

Attest:

RUTH C. MASON
*Attesting Officer*

C. MARSHALL DANN
*Commissioner of Patents and Trademarks*